US 6,551,621 B1

(12) United States Patent
Debregeas et al.

(10) Patent No.: US 6,551,621 B1
(45) Date of Patent: Apr. 22, 2003

(54) GASTROPROTECTED OMEPRAZOLE MICROGRANULES, METHOD FOR OBTAINING SAME AND PHARMACEUTICAL PREPARATIONS

(75) Inventors: Patrice Debregeas, Paris (FR); Gérard Leduc, Malesherbes (FR); Pascal Oury, Paris (FR); Pascal Suplie, Montaure (FR)

(73) Assignee: Ethypharm, Madrid (ES)

( * ) Notice: Subject to any disclaimer, the term of this patent is extended or adjusted under 35 U.S.C. 154(b) by 0 days.

(21) Appl. No.: 09/601,213

(22) PCT Filed: Aug. 10, 1998

(86) PCT No.: PCT/FR98/01783

§ 371 (c)(1),
(2), (4) Date: Oct. 13, 2000

(87) PCT Pub. No.: WO99/38511

PCT Pub. Date: Aug. 5, 1999

(30) Foreign Application Priority Data

Jan. 30, 1998 (FR) .............................................. 98 01098

(51) Int. Cl.⁷ .............................. A61K 9/16; A61K 9/50
(52) U.S. Cl. ....................... 424/493; 424/400; 424/451; 424/464; 424/472; 424/474; 424/489; 424/490

(58) Field of Search ................................ 424/489, 490, 424/493, 494, 497

(56) References Cited

U.S. PATENT DOCUMENTS 5,385,739 A * 1/1995 Debregeas et al. ......... 424/494

FOREIGN PATENT DOCUMENTS

| EP | 0 342 522 | 5/1989 |
| WO | WO 93/25204 | 12/1993 |
| WO | WO 96/01624 | 1/1996 |
| WO | WO 97/12581 | 4/1997 |
| WO | WO 98/19668 | 5/1998 |
| WO | WO 98/52564 | 11/1998 |

OTHER PUBLICATIONS

International Search Report for PCT/FR98/01783.

* cited by examiner

Primary Examiner—Thurman K. Page
Assistant Examiner—Charesse Evans
(74) Attorney, Agent, or Firm—Burns, Doane, Swecker & Mathis, LLP

(57) ABSTRACT

The invention concerns omeprazole microgranules each comprising an active layer containing the active principle, and an outer gastroprotecting layer containing a gastroprotecting agent, characterized in that the omeprazole is combined with at least a hydrophobic substance.

25 Claims, 3 Drawing Sheets

GASTROPROTECTED OMEPRAZOLE MICROGRANULES, METHOD FOR OBTAINING SAME AND PHARMACEUTICAL PREPARATIONS

The present invention relates to a pharmaceutical formulation of omeprazole in the form of gastroprotected microgranules having an improved stability over time.

The present invention additionally applies to the process for the manufacture of the said microgranules and to the pharmaceutical preparations containing them.

Omeprazole or 5-methoxy-2-[[(4-methoxy-3,5-dimethyl-2-pyridinyl)methyl]sulphinyl]-1-benzimidazole is known as a powerful inhibitor of acidic gastrointestinal secretion (Swedish Patent No. 78 04231) and can be used in the treatment of gastric and duodenal ulcers.

It is also known that omeprazole readily degrades in acidic medium and in neutral medium. The degradation half-life of omeprazole is ten minutes at a pH of less than 4, eighteen hours at a pH equal to 6.5 and approximately 300 days at a pH equal to 11.

For this reason, pharmaceutical dosage forms of omeprazole for oral administration are gastroprotected so that the active principle reaches the small intestine without being degraded.

During long-term storage under normal conditions of use (temperature of 25° C. and degree of humidity of the order of 40–75%), it has been observed that conventional formulations are not stable over time. The degradation of the omeprazole, the appearance of harmful degradation products and colouring of the formulation have been observed.

This is because the stability of omeprazole is also affected by moisture, heat, the presence of organic solvents, even in the form of traces, and, to a lesser extent, light. Organic solvents are generally used in the process for the manufacture of omeprazole formulations, which it is desired to avoid for ecological reasons.

In order to improve the duration of stability on storage of gastroprotected formulations comprising omeprazole or an alkaline salt of omeprazole, the active principle is often combined with an excipient, such as:

an alkaline substance (see Patent Application EP-247, 983), for example a sodium, potassium, calcium or aluminium salt of an organic acid, such as phosphoric acid, carbonic acid or citric acid, an antiacid substance, for example an aluminium, magnesium or calcium oxide or hydroxide, a pharmaceutically acceptable organic buffer substance, such as a basic amino acid or one of their salts, in particular trihydroxymethylaminomethane, an inert substance, such as mannitol (see Patent Application of EP-646,006) or titanium dioxide (see Patent Application WO 96/37 195), an agent which dehydrates, during the final packaging of the formulation.

However, it has been observed that the stability of the formulations of the prior art is unsatisfactory and the aim of the present invention is to provide a gastroprotected formulation of omeprazole microgranules which is stable to coloration, the stability to long-term storage of which is improved and which additionally exhibits the desired therapeutic properties, that is to say a degree of resistance to dissolution in acidic medium and rapid solubility in neutral medium.

The object of the present invention is thus to provide gastroprotected microgranules of omeprazole which exhibit dissolution profiles corresponding to the targeted therapeutic application and which are advantageously stable over time.

The present invention relates to a novel gastro-protected formulation of omeprazole comprising at least one hydrophobic substance chosen in order to increase the stability of the active principle while obtaining the desired dissolution profile. The Applicant Company has in particular optimized the composition of such a formulation by selecting combinations of several hydrophobic substances in order to achieve the objective of the present invention.

The microgranules of omeprazole which are the subject-matter of the present invention are advantageously devoid:

of alkaline compounds in the form of salts, of ionic surface-active agents, such as the lauryl sulphate commonly used to stabilize omeprazole, and of traces of organic solvents.

The microgranules of omeprazole according to the invention each comprise an active layer comprising the active principle and an external gastroprotective layer comprising a gastroprotection agent and are characterized in that they comprise at least one hydrophobic substance.

Hydrophobic substances will be chosen which do not react chemically with omeprazole, which can be easily employed during formulation, which are compatible with the excipients used and which make it possible to obtain the dissolution and release profiles desired for the targeted therapeutic application.

In the active layer, the hydrophobic substance preferably represents between 5 and 40% by weight of the omeprazole.

In a preferred embodiment, the active layer comprising the omeprazole is advantageously coated with at least one protective layer.

This protective layer can comprise a diluent substance or a coating agent in combination with a hydrophobic plasticizer.

The gastroprotection agent can be combined, in the external gastroprotective layer, with a hydrophobic agent preferably chosen from glycerides.

According to a particularly advantageous embodiment, the microgranules according to the invention use a combination of different hydrophobic agents which makes it possible to improve the stability of the formulation.

According to a preferred embodiment, the microgranules according to the invention comprise:

a layer of active principle comprising omeprazole, a binder chosen from any pharmaceutically acceptable binder, a hydrophobic substance and a substance which dissolves the active principle, a first protective layer comprising one or more pharmaceutically acceptable diluent substances and a binder chosen from any pharmaceutically acceptable binder, a second hydrophobic protective layer comprising a coating agent and a hydrophobic plasticizer, a gastroprotective layer comprising an enteric film-forming agent, a plasticizer and a hydrophobic substance.

The layer of active principle advantageously comprises a hydrophobic substance of the fatty substance type advantageously chosen from silicone oils: it preferably represents between 5 and 40% of the weight of active principle.

A non-ionic surfactant, preferably chosen from polysorbates (Montanox 80® or Montane 20–60®), is also included in this layer in a proportion of 5 to 15% with respect to the weight of active principle.

The active layer advantageously comprises a binder chosen from pharmaceutically acceptable binders, in this case hydroxypropylmethylcellulose, the proportion by mass of which represents 30 to 50% with respect to the weight of active principle.

The first protective layer advantageously comprises an inert substance chosen particularly from pharmaceutically acceptable diluents, including mannitol (which is non-hygroscopic), in a proportion by mass of 100 to 300% and preferably 200% of the weight of the active principle.

This layer also comprises a binder chosen from pharmaceutically acceptable binders, advantageously hydroxypropylmethylcellulose, in a proportion of 10 to 30% and preferably 20% of the weight of mannitol.

It is optionally possible to include, in this protective layer, a lubricant chosen from pharmaceutically acceptable lubricants, in this case talc (which is non-hygroscopic), in a proportion of 0 to 100% of the weight of the active principle.

The second protective layer is composed of a water-soluble coating agent chosen from pharmaceutically acceptable film-forming agents and advantageously hydroxypropylmethylcellulose, in a proportion of 1 to 10%, preferably 5%, of the weight of microgranules obtained after coating on the first protective layer.

Use will advantageously be made, in the second protective layer, of a hydrophobic plasticizer, such as Myvacet®, in a proportion of 10 to 30% of the dry varnish of the coating agent used.

Use will optionally be made of a lubricating agent chosen from pharmaceutically acceptable lubricants, advantageously talc (which is non-hygroscopic), in a proportion of 10 to 50%, preferably 15%, of the dry varnish of the coating agent used.

The external gastroprotective layer comprises a gastroprotective film-forming agent, advantageously a methacrylic acid copolymer, such as Eudragit L30D®, in a proportion of 15 to 30%, preferably 20%, of polymer, on a dry basis, with respect to the mass of microgranules which is treated.

There will advantageously be included, with the gastroprotective film-forming agent, one or more hydrophobic substances chosen from the waxes and oils often used in the pharmaceutical industry, preferably Gélucire 50–13®, in a proportion of 5 to 20% of the dry varnish of the film-forming agent used.

Use can optionally be made, for the external gastroprotective layer, of a plasticizer chosen from pharmaceutically acceptable plasticizers, preferably triethyl citrate, representing from 5 to 20%, advantageously 10%, of the weight of dry varnish of the film-forming agent used.

Use will optionally be made, in order to reinforce the resistance to moisture of the gastroprotective layer, of a lubricating agent chosen from pharmaceutically acceptable lubricants, advantageously talc.

According to a preferred embodiment of the present invention, the active layer is coated on a neutral core composed, for example, of sucrose and starch, the diameter of which is between 700 and 900 microns.

The microgranules according to the invention will preferably have a particle size of between 0.5 and 3 mm, more preferably between 0.7 and 2 mm.

Another subject-matter of the present invention is a process for the preparation of the microgranules according to the invention. This process is characterized in that it is carried out in aqueous medium, without using any organic solvent.

The microgranules described in the present invention will be obtained by using any appliance appropriate for the preparation and the coating of microgranules which is well known to a person skilled in the art and, in particular, appliances of conventional turbomixer, perforated turbomixer or fluidized air bed type.

According to a preferred embodiment, the microgranules according to the invention are obtained by coating on a neutral core, preferably in a fluidized air bed, by successively spraying:

an aqueous suspension of omeprazole and a hydrophobic substance, optionally an aqueous suspension of a diluent substance, and/or an aqueous suspension of a coating agent and a hydrophobic plasticizer, and an aqueous suspension of the gastroprotection agent, also known as enteric film-forming agent.

According to a very particularly valued embodiment, the microgranules according to the invention are coated on a neutral core, in a fluidized air bed, by successively spraying:

an aqueous suspension of omeprazole and a silicone oil, an aqueous suspension of mannitol, an aqueous suspension of hydroxypropylcellulose, and an aqueous suspension of the gastroprotection agent.

Each spraying stage is advantageously followed by sieving and drying at a temperature below the melting temperature of each of the compounds forming part of the composition of the microgranules at the said stage.

The microgranules obtained according to this process advantageously comprise less than 1.5%, preferably 0.5%, by weight of water.

Finally, a subject-matter of the present invention is the pharmaceutical preparations comprising the microgranules according to the invention which are capable of being obtained by the process described above; these preparations will advantageously be in the form of gelatin capsules comprising 5 to 60 mg approximately of omeprazole.

Other characteristics and advantages of the present invention will become apparent in the light of the examples and figures hereinbelow.

EXAMPLE 1

Figure 1:
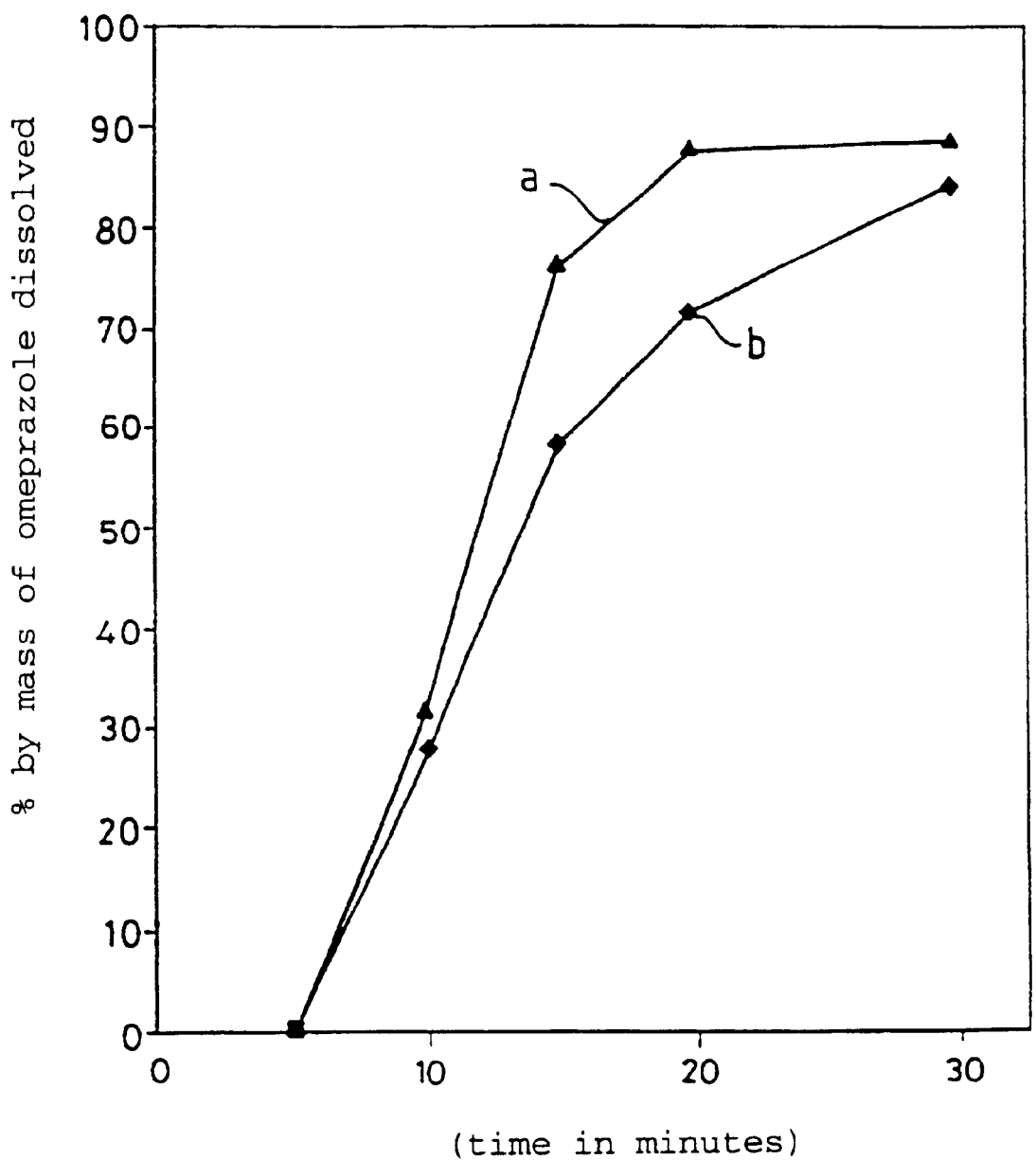
FIG. 1 represents the in vitro dissolution curve at pH 6.8 of gelatin capsules according to the invention (curve a) compared with that of an oral omeprazole formulation of the prior art (curve b).
Figure 2:
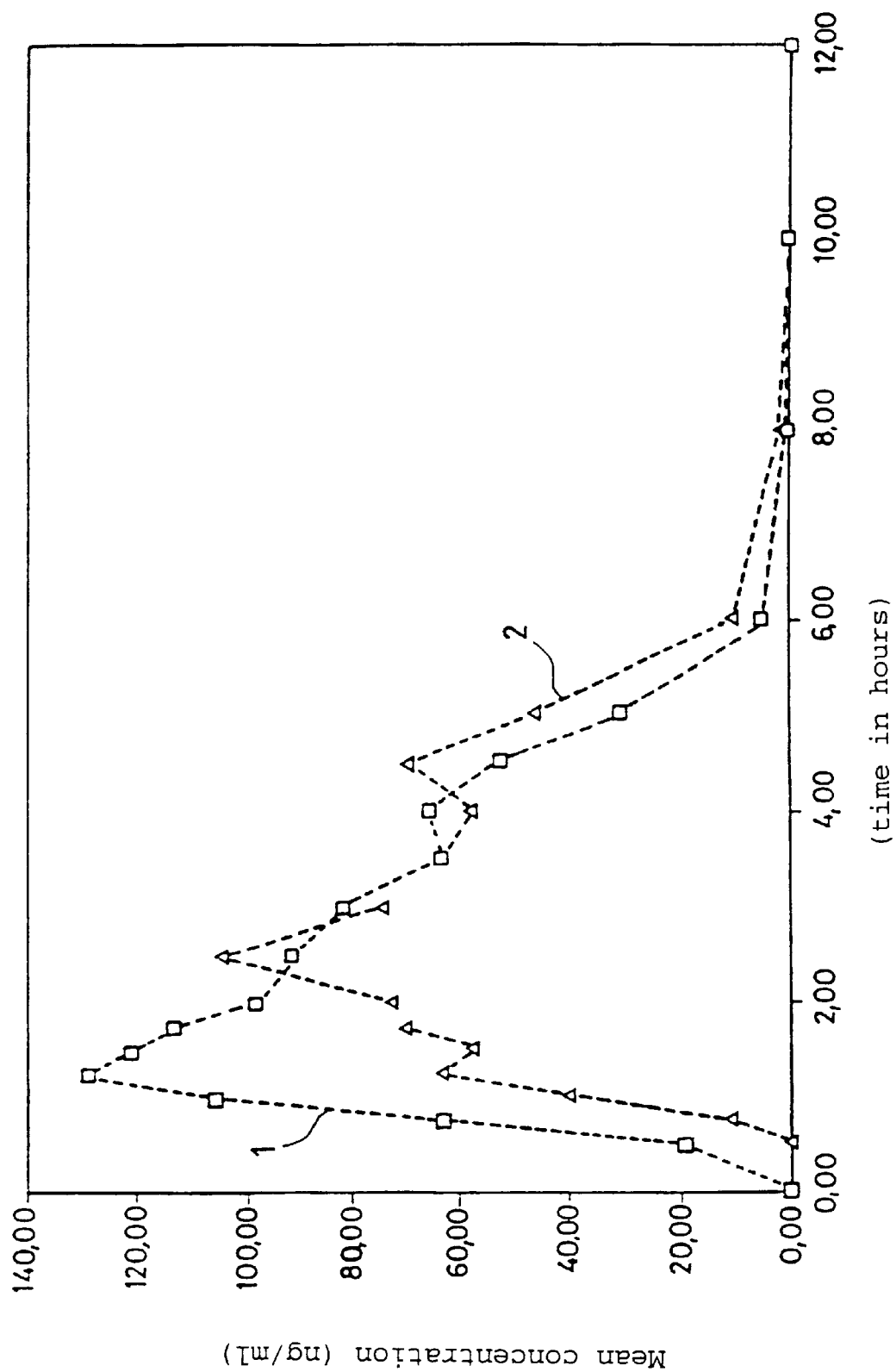
FIG. 2 represents the in vivo dissolution curve of gelatin capsules according to the invention (curve 1) compared with that of an oral omeprazole formulation of the prior art (curves 2).

Microgranules are prepared in a fluidized air bed device of Ohlman type.

a) Coating the [Lacuna] Principle

A suspension of the active principle is prepared which has the following composition.

| Composition of the suspension of active principle | % by mass |
|---|---|
| Omeprazole | 14.9 |
| Pharmacoat 603 ® | 5.9 |
| Dimethicone | 4.2 |
| Polysorbate 80 ® | 1.5 |
| Purified water | 73.5 |

The purified water is stirred and the Pharmacoat 603® (manufactured by Seppic), the Polysorbate 80® (manufactured by Seppic), the Dimethicone (manufactured by Lambert and Rivière) and the omeprazole are successively added.

Stirring of the suspension is maintained throughout the coating of the Neutres 20® (manufactured by NP Pharm) placed in the fluidized air bed.

The coated Neutres® are subsequently sieved and dried for four hours at approximately 50° C.

b) Pharmacoat®/Mannitol Precoating

A precoating suspension is prepared consisting of 4% by weight of Pharmacoat 603®, 20% by weight of Mannitol 25® (both manufactured by Roquette) and 76% of purified water.

The coated and dried Neutres obtained above are sprayed with this precoating suspension.

The precoated Neutres are subsequently sieved and then dried for one to four hours at approximately 50° C.

c) Pharmacoat®/Myvacet® Precoating

A precoating suspension is prepared with the following composition.

| Composition of the precoating suspension | % by mass |
|---|---|
| Pharmacoat 603 ® | 7.14 |
| Myvacet 0.45 ® | 1.79 |
| Talc | 1.79 |
| Purified water | 89.28 |

This precoating stage is carried out under the same conditions as the Pharmacoat®/Mannitol precoating stage.

During stages a), b) and c), the temperature of the granules is maintained between 26 and 28° C. during the spraying of the suspension.

d) Eudragit L30D®/Gélucire®Coating

A coating suspension is prepared with the following composition:

| Composition of the coating suspension | % by mass |
|---|---|
| Eudragit L30D ® | 54.64 |
| Triethyl citrate | 1.64 |
| Gelucire 5013 ® | 1.64 |
| Purified water | 42.08 | molten Gélucire® (manufactured by Gattefosse) being added at 50° C.

The coated microgranules are subsequently sieved and dried at approximately 45° C. for four hours and then lubricated with talc.

The losses on drying of the microgranules are of the order of 0.5 to 1% after fifteen minutes at 95° C., at the end of each of stages a) to d).

EXAMPLE 2

Microgranules are prepared according to the process of Example 1, in order to obtain the following formulations A and B.

| | Percentage by mass | |
|---|---|---|
| Composition | Formulation A | Formulation B |
| Neutres 20 ® | 47.5 | 36.2 |
| Omeprazole | 7.9 | 9.0 |
| Pharmacoat 630 ® | 9.1 | 11.2 |
| Dimethicone | 0.8 | 0.9 |
| Polysorbate 80 ® | 0.8 | 0.9 |
| Mannitol 25 | 12.0 | 20.3 |
| Myvacet 9.45 V | 0.9 | 0.9 |
| Talc | 0.9 | 1.2 |
| Eudragit L30D ® | 16.6 | 16.2 |
| Triethyl citrate | 1.6 | 1.6 |
| Gelucire 5013 ® | 1.6 | 1.6 |
| | Formulation A | Formulation B |
| Content (mg/g) | 71 | 88 |
| Gastroresistance test (Percentage by mass) | | |
| after 2 h at pH 1.2 | 1.8 | 1.4 |
| then for 30 min at pH 6.8 | 88.3 | 86 |

In accordance with the European Pharmacopoeia, the in vitro dissolution tests are carried out, with a device with a paddle rotating at a rate of 100 revolutions/minute, in 750 ml of water at 37° C.±0.5° C. and pH=1.2, to which is added, after two hours, after having carried out the standard, 250 ml of an aqueous solution of $Na_3PO_4$ at pH=12.5, in order to obtain 1l of a solution at pH=6.8.

Stability Studies

The stability of the unpackaged formulation A over time under actual storage conditions (i.e. at 25° C. and 40% relative humidity) is evaluated.

| Formulation A | t = 0 | t = 11 months |
|---|---|---|
| Gastroresistance test (%) | | |
| after 2 h at pH 1.2 | 4.6 | 1.4 |
| then for 30 min at pH 6.8 | 96.3 | 94.1 |
| Content of impurities (%) | 0.4 | 0.4 |
| Colour | off white | off white |

The microgranules A and B prepared in Example 2 are packaged in gelatin capsules of size 2, respectively recorded as $G_A$ and $G_B$.

A first study is carried out under accelerated ageing conditions, according to a standardized ICH test (at 40° C. and 75% relative humidity). The stability tests as a function of time on the gelatin capsules $G_A$ and $G_B$ are carried out by placing the gelatin capsules in opaque polyethylene bottles.

The impurities are quantitatively determined by U.V. spectrometry after separation by high performance liquid chromatography.

The gastroresistance tests are carried out under the same conditions as in Example 2 and must verify the following standard in order to be judged positive:

10% or less after two hours at pH 1.2 and more than 75% after thirty minutes at pH 6.8.

The quantitative determination of active principle and the water content are respectively carried out according to the standards USP <905> and USP <921>.

The stability results of the gelatin capsules $G_A$ and $G_B$ under accelerated ageing condition are summarized respectively in Tables 1 and 2.

TABLE 1

| $G_A$ | t = 0 | 1 month | 2 months | 3 months |
|---|---|---|---|---|
| Quantitative determination (mg/gelatin capsule) | 14 | 14.2 | 14.2 | 11.8 |
| Gastroresistance test (%) | | | | |
| after 2 h at pH 1.2 | 4.6 | 0.0 | 2.0 | 3.3 |
| then for 30 min at pH 6.8 | 96.3 | 90.2 | 86.3 | 94.0 |
| Water content (%) | 1.4 | 2.0 | 1.8 | 1.9 |
| Content of impurities (%) | 0.4 | 1.0 | 2.7 | 10.2 |
| Colours | off white | off white | grey | grey |

TABLE 2

| $G_B$ | t = 0 | 1 month | 2 months |
|---|---|---|---|
| Quantitative determination (mg/gelatin capsule) | 20 | 19.7 | 19.9 |
| Gastroresistance test (%) | | | |
| after 2 h at pH 1.2 | 2 | 2.4 | 2.5 |
| then for 30 min at pH 6.8 | 92.4 | 91.9 | 92.4 |
| Water content (%) | 0.8 | 1.4 | 1.1 |
| Content of impurities (%) | 0.3 | 4.5 | 4.8 |
| Colour | off white | off white | off white and grey highlights |

A comparative study on the stability of the microgranules $G_A$ and of a formulation of the prior art is subsequently carried out, still under accelerated ageing conditions.

Table 3 shows the increased stability of the microgranules according to the present invention with respect to a formulation of the prior art sold by the company Astra under the trade name Mopral® (Patent EP-247,983).

TABLE 3

| | t = 0 | 1 month | 2 months | 3 months |
|---|---|---|---|---|
| Content of impurities (%) | | | | |
| Mopral ® | — | 1.06 | 22.6 | 38.17 |
| $G_A$ | 0.4 | 1.0 | 2.7 | 10.2 |
| Colours | | | | |
| Mopral ® | — | brown | brown | brown |
| $G_B$ | off white | off white | grey | grey |

Clinical Trials

These trials are aimed at confirming that the formulations according to the invention do not cause a loss in bioavailability.

A first study is carried out by comparing the bioavailability parameters of a formulation according to the invention, recorded as A1, and of a formulation of the prior art, recorded as B, sold under the trade name Losec® by the company Astra.

This randomized study is carried out on 10 patients, to whom is administered a single dose of 20 mg of microgranules according to the invention. The plasma concentration of omeprazole is monitored during the eight hours following administration.

After a resting period of 7 days, these same ten patients receive a single dose of 20 mg of a formulation of the [lacuna] art B. In the same way, the plasma concentration of omeprazole is measured regularly during the eight hours following administration.

Figure 3:
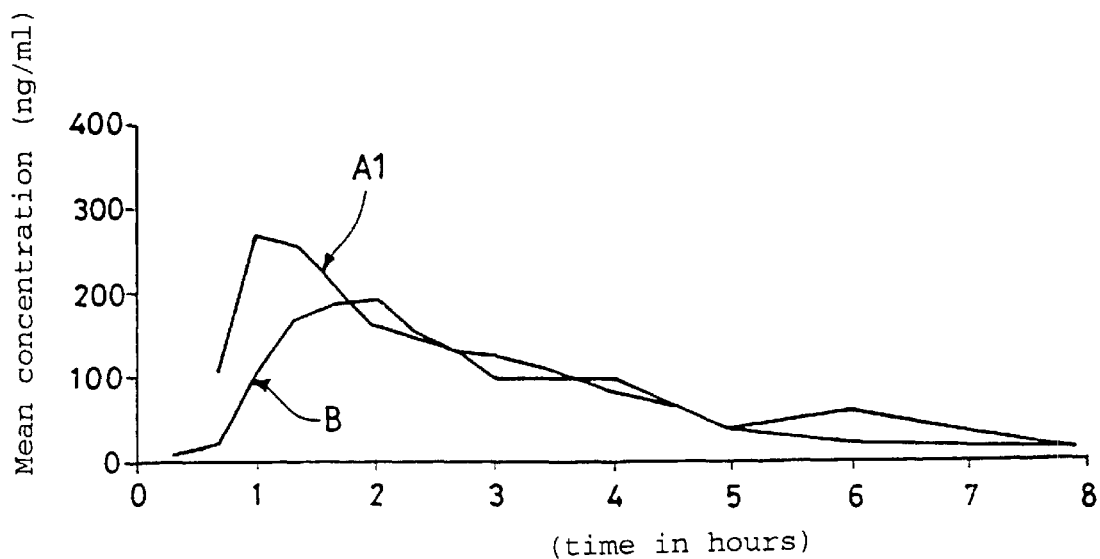
FIG. 3 represents the change over time of the mean plasma concentration of omeprazole in 10 patients, to whom a formulation of the invention was administered (curve A1), and in the same 10 patients, to whom a formulation of the prior art was administered (curve B).

The change in the mean plasma concentration of omeprazole (measured with respect to the 10 patients), calculated for A1 and then for B, are represented in FIG. 3.

Table 4 gives the mean value of the main bioavailability parameters corresponding to the two curves A1 and B.

TABLE 4

| Treatment | $AUC_{o-t}$ (ng/ml) | $AUC_{inf}$ (ng/ml) | $C_{max}$ (ng/ml) | $T_{max}$ (h) | $K_{el}$ | $T_{1/2}$ (h) |
|---|---|---|---|---|---|---|
| A1 | 544.7 | 618.6 | 336.3 | 2.68 | 0.097 | 0.76 |
| Coefficient of variation | (48%) | (42%) | (37%) | (63%) | (31%) | (29%) |
| B | 517.5 | 554.1 | 291.1 | 2.26 | 1.00 | 0.75 |
| Coefficient of variation | (57%) | (55%) | (42%) | (44%) | (29%) | (32%) |
| A1/B ratio | 98% | 94% | 83% | — | — | — |

A second study is carried out under the same conditions as above by administering a formulation according to the invention, recorded as A2, and then a formulation of the prior art, recorded as C, sold under the trade name Prilosec® by the company Merck.

Figure 4:
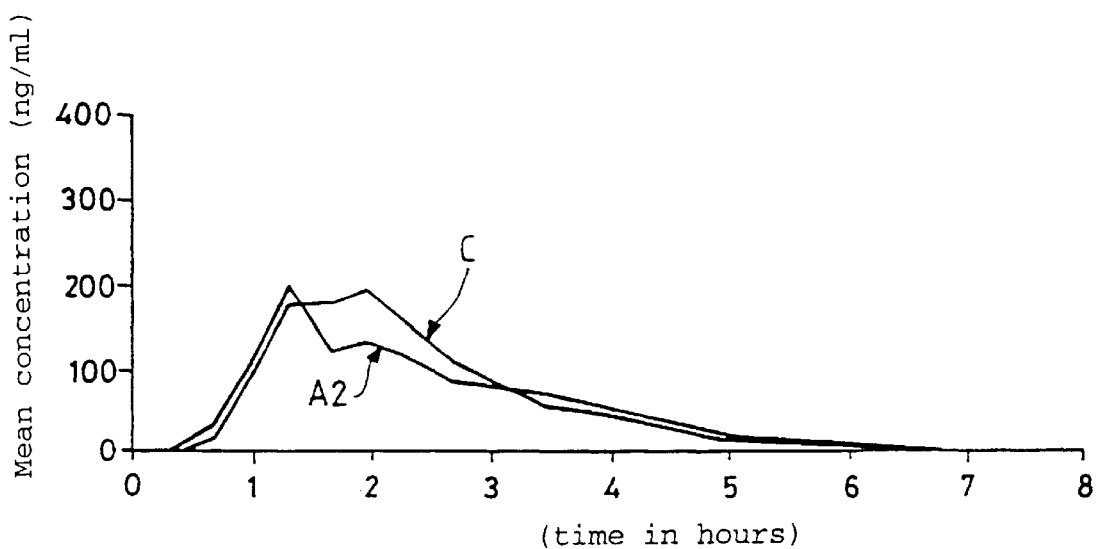
FIG. 4 represents the change over time of the mean plasma concentration of omeprazole in 10 patients, to whom a formulation of the invention was administered (curve A2), and in the same 10 patients, to whom a formulation of the prior art was administered (curve C).

The change over time in the mean plasma concentration of omeprazole in the 10 patients, measured for A2 and C, is represented in FIG. 4.

Table 5 gives the mean value of the main bioavailability parameters corresponding to the two curves A2 and C.

TABLE 5

| Treatment | $AUC_{o-t}$ (ng/ml) | $AUC_{inf}$ (ng/ml) | $C_{max}$ (ng/ml) | $T_{max}$ (h) | $K_{el}$ | $T_{1/2}$ (h) |
|---|---|---|---|---|---|---|
| A2 | 423.2 | 431.9 | 274.6 | 2.38 | 1.11 | 0.63 |
| Coefficient of variation | (48%) | (56%) | (51%) | (46%) | (13%) | (14%) |
| C | 429.0 | 459.8 | 283.6 | 1.95 | 1.07 | 0.67 |
| Coefficient of variation | (41%) | (40%) | (51%) | (50%) | (21%) | (25%) |
| A2/C ratio | 117% | 112% | 107% | — | — | — |

What is claimed is:

1. Omeprazole microgranules, each comprising an active layer comprising the active principle and an external gastroprotective layer comprising a gastroprotective agent, characterized in that they are devoid of alkaline compounds in the form of salts and that the active layer comprises a hydrophobic substance.

2. Microgranules according to claim 1, characterized in that the active layer comprises a hydrophobic substance which represents 5 to 40% by weight of omeprazole.

3. Microgranules according to claim 1 or 2, characterized in that the active layer is coated with at least one protective layer.

4. Microgranules as claimed in claim 1, wherein the protective layer comprises a diluent substance or a coating agent in combination with a hydrophobic plasticizer.

5. Microgranules as claimed in claim 1, wherein the external gastroprotective layer, a hydrophobic agent is used in combination with the gastroprotection agent.

6. Microgranules, wherein each microgranule comprises
(A) a layer of active principle comprising omeprazole, a binder chosen from any pharmaceutically acceptable binder, a hydrophobic substance and a solubilizing substance;

(B) a first protective layer comprising one or more pharmaceutically acceptable diluent substances and a binder;

(C) a second hydrophobic protective layer comprising a coating agent and a hydrophobic plasticizer; and (D) a gastroprotective layer comprising an enteric film-forming agent, a plasticizer, and a hydrophobic substance.

7. Microgranules as claimed in claim 6, wherein the hydrophobic substance comprised within the active layer is chosen from silicone oils.

8. Microgranules as claimed in claim 6, wherein the solubilizing substance is a non-ionic surfactant chosen from polysorbates.

9. Microgranules as claimed in claim 6, wherein the binder is hydroxypropylmethyl-cellulose.

10. Microgranules as claimed in claim 6, wherein the first protective layer comprises mannitol as diluent substance.

11. Microgranules as claimed in claim 6, wherein the second protective layer is composed of a coating agent and of a hydrophobic plasticizer.

12. Microgranules as claimed in claim 6, wherein the hydrophobic substance comprised within the gastroprotective layer is chosen from glycerides.

13. Microgranules as claimed in claim 1 or 6, wherein the active layer is coated on a neutral core and in that the particle size of the microgranules is between 0.5 and 3 mm.

14. A process for the preparation of the microgranules as claimed in claim 1 or 6, wherein the process is carried out in aqueous medium.

15. The process as claimed in claim 14, wherein a coating operation is carried out in a fluidized air bed.

16. Pharmaceutical preparations comprising the microgranules as claimed in claim 1 or 6, comprising 5 to 60 mg approximately of omeprazole.

17. The microgranules as claimed in claim 11, wherein the coating agent is hydroxypropylmethylcellulose.

18. A composition comprising 36.2% by mass neutral core, 9.0% by mass omperazole, 11.2% by mass hydroxypropylmethylcellulose, 0.9% by mass dimethicone, 0.9% by mass polysorbate, 20.3% by mass mannitol 25, 0.9% by mass diacylated monoglyceride, 1.2% by mass talc, 16.2% by mass methacrylic acid copolymer, 1.6% by mass triethyl citrate, and 1.6% by mass glyceride.

19. The microgranules as claimed in claim 11, wherein the hydrophobic plasticizer is diacetylated monoglyceride.

20. The microgranule as claimed in claim 6, wherein the active layer comprises a hydrophobic substance which represents 5 to 40% by weight of omperazole.

21. Microgranules as claimed in claim 1 or 2 wherein the hydrophobic substance is chosen from silicon oils.

22. Microgranules as claimed in claim 4, wherein the diluent substance is chosen from mannitol.

23. Microgranules as claimed in claim 4, wherein the coating agent is chosen from hydroxypropylmethylcellulose.

24. Microgranules as claimed in claim 4, wherein the hydrophobic plasticizer is chosen from diacylated monoglyceride.

25. Microgranules as claimed in claim 5, wherein the hydrophobic agent is chosen from glycerides.

* * * * *

UNITED STATES PATENT AND TRADEMARK OFFICE
CERTIFICATE OF CORRECTION

PATENT NO. : 6,551,621 B1  Page 1 of 1
DATED : April 22, 2003
INVENTOR(S) : Patrice Debregeas et al.

It is certified that error appears in the above-identified patent and that said Letters Patent is hereby corrected as shown below:

<u>Column 10,</u>
Line 7, replace "omperazole" with -- omeprazole --;
Line 10, replace "diacylated" with -- diacetylated --;
Line 17, replace "omperazole" with -- omeprazole --; and
Line 26, replace "diacylated" with -- diacetylated --.

Signed and Sealed this

Eighteenth Day of May, 2004

JON W. DUDAS
*Acting Director of the United States Patent and Trademark Office*